(12) United States Patent
Rudraraju et al.

(10) Patent No.: US 11,232,852 B2
(45) Date of Patent: Jan. 25, 2022

(54) TECHNOLOGIES FOR NUCLEOTIDE SEQUENCE SCREENING

(71) Applicant: Battelle Memorial Institute, Columbus, OH (US)

(72) Inventors: Sachin Rudraraju, Powell, OH (US); Omar P. Tabbaa, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 16/705,191

(22) Filed: Dec. 5, 2019

(65) Prior Publication Data

US 2020/0185061 A1 Jun. 11, 2020

Related U.S. Application Data

(60) Provisional application No. 62/776,273, filed on Dec. 6, 2018.

(51) Int. Cl.
*G16B 30/10* (2019.01)
*G16H 10/40* (2018.01)
*G16B 35/20* (2019.01)

(52) U.S. Cl.
CPC ............ *G16B 30/10* (2019.02); *G16B 35/20* (2019.02); *G16H 10/40* (2018.01)

(58) Field of Classification Search
None
See application file for complete search history.

(56) References Cited

U.S. PATENT DOCUMENTS 6,005,566 A * 12/1999 Jones ................ G06F 9/451
715/788
2012/0035857 A1 2/2012 Stenger et al.
2013/0166221 A1 6/2013 Inglis et al.
2014/0304290 A1* 10/2014 Brettin ................ G16B 50/00
707/758
2017/0357752 A1 12/2017 Diggans

OTHER PUBLICATIONS

Adam et al. Strengths and limitations of the federal guidance on synthetic DNA Nature Biotechnology vol. 29, pp. 208-210 (Year: 2011).*
Caruthers A brief review of DNA and RNA chemical synthesis Biochemical Society Transactions vol. 39 pp. 579-580 (Year: 2011).*
International Search Report and Written Opinion for related PCT/US2019/064795, dated Feb. 21, 2020, 20 pages.
Altschul, Stephen F., et al., "Basic Local Alignment Search Tool," J. Mol. Biol. (1990) 215, 403-410 (8 pages).

* cited by examiner

*Primary Examiner* — John S Brusca
(74) *Attorney, Agent, or Firm* — Barnes & Thornburg LLP

(57) ABSTRACT

Illustrative embodiments of technologies for nucleotide sequence screening are disclosed. In one illustrative embodiment, a system may include a server to communicate with a remote frontend over a network in order to receive a request to screen one or more nucleotide sequences for hazardous content and to report a result of the screening. The system may also include a compute engine to compare each nucleotide sequence to each of a plurality of reference sequences stored in a reference database, to detect whether hazardous content is present in each nucleotide sequence based upon the comparison of that nucleotide sequence to each of the plurality of reference sequences, and to assign one of a plurality of threat levels to each nucleotide sequence based upon the detection of whether hazardous content is present in that nucleotide sequence. The reported result may include the threat level assigned to each nucleotide sequence.

26 Claims, 3 Drawing Sheets

TECHNOLOGIES FOR NUCLEOTIDE SEQUENCE SCREENING

CROSS-REFERENCE TO RELATED APPLICATION

This application claims the benefit of U.S. Provisional Patent Application No. 62/776,273, filed Dec. 6, 2018, the entire disclosure of which is incorporated herein by reference.

TECHNICAL FIELD

The present disclosure relates, generally, to nucleotide sequence screening and, more particularly, to technologies for screening nucleotide sequences for indications of hazardous content.

BACKGROUND

Gene synthesis, sometimes referred to as DNA printing, involves the creation of artificial genes "de novo," without the need for preexisting, template DNA sequences. Gene synthesis approaches are most often based on a combination of organic chemistry and molecular biology techniques. Gene synthesis is an important tool in many fields of recombinant DNA technology, including heterologous gene expression, vaccine development, gene therapy and molecular engineering. The synthesis of nucleic acid sequences can be more economical than classical cloning and mutagenesis procedures. It is also a powerful and flexible engineering tool for creating and designing new DNA sequences and protein functions.

Commercial gene synthesis carries risk in that the synthesizing party typically receives the requested sequence from a third party client and is unaware of the contents of the sequence to be synthesized. Whether known or unknown to the client, it is possible that the requested sequence may contain hazardous content, such as genes relating to disease or biological weapons, by way of example. Lacking any technology for accurately and efficiently checking unknown sequences for hazardous content, however, the synthesizing party is unable to evaluate the risk of synthesizing the requested sequence up front. More generally, any party dealing with an unknown nucleotide sequence may benefit from an improved solution for screening the contents of that sequence (for hazardous content or otherwise).

SUMMARY

The following clauses, and combinations thereof, provide various illustrative aspects of the inventions described herein. The various illustrative embodiments described in any other section of this patent application, including the section titled "DETAILED DESCRIPTION OF THE DRAWINGS," are applicable to any of the following embodiments of the inventions described in the numbered clauses below.

1. A system comprising a server to communicate with a remote frontend over a network to receive, from the frontend, a request to screen one or more nucleotide sequences for hazardous content and to report, to the frontend, a result of screening the one or more nucleotide sequences for hazardous content.

2. The system of clause 1, further comprising a compute engine to compare each nucleotide sequence of the one or more nucleotide sequences to each of a plurality of reference sequences stored in a reference database, to detect whether hazardous content is present in each nucleotide sequence based upon the comparison of that nucleotide sequence to each of the plurality of reference sequences, and to assign one of a plurality of threat levels to each nucleotide sequence based upon the detection of whether hazardous content is present in that nucleotide sequence.

3. The system of clause 2, wherein the result reported to the frontend by the server comprises the threat level assigned to each nucleotide sequence of the one or more nucleotide sequences.

4. The system of any one of clauses 2 and 3, wherein the plurality of threat levels includes at least a first level representing a threat, a second level representing a potential threat, a third level representing an unlikely threat, and a fourth level representing a non-threat.

5. The system of any one of clauses 2-4, wherein to compare each nucleotide sequence of the one or more nucleotide sequences to each of the plurality of reference sequences comprises using a basic local alignment search tool (BLAST) to compare each nucleotide sequence to each of the plurality of reference sequences.

6. The system of any one of clauses 2-5, wherein each of the plurality of reference sequences includes hazardous content.

7. The system of clause 6, wherein the reference database further comprises metadata associated with each reference sequence that describes one or more characteristics of the hazardous content included in that reference sequence.

8. The system of clause 7, wherein the compute engine is further to retrieve the corresponding metadata from the reference database in response to detecting that hazardous content is present in one of the nucleotide sequences.

9. The system of clause 8, wherein the result reported to the frontend by the server comprises the corresponding metadata for each nucleotide sequence for which hazardous content is detected.

10. The system of any one of clauses 2-9, wherein to detect whether hazardous content is present in each nucleotide sequence based upon the comparison of that nucleotide sequence to each of the plurality of reference sequences comprises to select a reference sequence that provided a closest match to that nucleotide sequence during the comparison of that nucleotide sequence to each of the plurality of reference sequences, wherein the selected reference sequence includes hazardous content.

11. The system of clause 10, wherein to detect whether hazardous content is present in each nucleotide sequence based upon the comparison of that nucleotide sequence to each of the plurality of reference sequences further comprises to detect that hazardous content is present in that nucleotide sequence in response to determining that (i) a matching length between the selected reference sequence and that nucleotide sequence exceeds a threshold length and (ii) a matching percentage between the selected reference sequence and that nucleotide sequence exceeds a threshold percentage.

12. The system of any one of clauses 2-11, wherein to detect whether hazardous content is present in each nucleotide sequence based upon the comparison of that nucleotide sequence to each of the plurality of reference sequences comprises to, for each reference sequence including hazardous content where (i) a matching length between the reference sequence and that nucleotide sequence does not exceed a threshold length but (ii) a matching percentage between the reference sequence and that nucleotide sequence does exceed a threshold percentage, extending the matching length up to the threshold length.

13. The system of clause 12, wherein to detect whether hazardous content is present in each nucleotide sequence based upon the comparison of that nucleotide sequence to each of the plurality of reference sequences further comprises to detect that hazardous content is present in that nucleotide sequence in response to determining that the matching percentage between the extended reference sequence and that nucleotide sequence still exceeds the threshold percentage.

14. The system of any one of clauses 2-13, wherein to detect whether hazardous content is present in each nucleotide sequence based upon the comparison of that nucleotide sequence to each of the plurality of reference sequences comprises to, for each reference sequence including hazardous content where (i) a matching length between the reference sequence and that nucleotide sequence does exceed a threshold length but (ii) a matching percentage between the reference sequence and that nucleotide sequence does not exceed a threshold percentage, apply a sliding window to analyze a matching percentage between that nucleotide sequence and each portion of the reference sequence having the threshold length.

15. The system of clause 14, wherein to detect whether hazardous content is present in each nucleotide sequence based upon the comparison of that nucleotide sequence to each of the plurality of reference sequences further comprises to detect that hazardous content is present in that nucleotide sequence in response to determining that the matching percentage between that nucleotide sequence and any portion of the reference sequence having the threshold length exceeds the threshold percentage.

16. The system of any one of clauses 2-15, wherein to detect whether hazardous content is present in each nucleotide sequence based upon the comparison of that nucleotide sequence to each of the plurality of reference sequences comprises to select a plurality of nucleotide sequence segments that each matched part of one of the plurality of reference sequences including hazardous content, where a matching length between each selected nucleotide sequence segment and the corresponding partial reference sequence does not exceed a threshold length.

17. The system of clause 16, wherein to detect whether hazardous content is present in each nucleotide sequence based upon the comparison of that nucleotide sequence to each of the plurality of reference sequences further comprises to combine the selected plurality of nucleotide sequence segments into a composite nucleotide sequence.

18. The system of clause 17, wherein to detect whether hazardous content is present in each nucleotide sequence based upon the comparison of that nucleotide sequence to each of the plurality of reference sequences further comprises to apply a sliding window to the composite nucleotide sequence to analyze a matching percentage between each portion of the composite nucleotide sequence having the threshold length and the one of the plurality of reference sequences.

19. The system of clause 18, wherein to detect whether hazardous content is present in each nucleotide sequence based upon the comparison of that nucleotide sequence to each of the plurality of reference sequences further comprises to detect that hazardous content is present in the composite nucleotide sequence in response to determining that the matching percentage between any portion of the composite nucleotide sequence having the threshold length and the one of the plurality of reference sequences exceeds a threshold percentage.

20. The system of any one of clauses 1-19, wherein the frontend is to provide a graphical user interface to allow a user to input the one or more nucleotide sequences to be screened for hazardous content and to display to the user the result of screening the one or more nucleotide sequences for hazardous content.

21. The system of clause 20, wherein the graphical user interface is configured to allow the user to input a plurality of nucleotide sequences to be screened by uploading a single file containing the plurality of nucleotide sequences.

22. The system of any one of clauses 20 and 21, wherein the graphical user interface is configured to display to the user a progress of the screening of the one or more nucleotide sequences for hazardous content, based upon asynchronous updates received from the server, until the result is received from the server.

23. The system of any one of clauses 1-22, further comprising a workflow database including a queue of nucleotide sequences to be screened for hazardous content, wherein the server is further to write each of the one or more nucleotide sequences received from the frontend to the queue, and wherein the compute engine is further to read one nucleotide sequence at a time from the queue in order to compare that nucleotide sequence to each of the plurality of reference sequences.

24. A method comprising receiving, with a server from a remote frontend over a network, a request to screen one or more nucleotide sequences for hazardous content.

25. The method of clause 24, further comprising comparing, with a compute engine, each nucleotide sequence of the one or more nucleotide sequences to each of a plurality of reference sequences stored in a reference database.

26. The method of clause 25, further comprising detecting, with the compute engine, whether hazardous content is present in each nucleotide sequence based upon the comparison of that nucleotide sequence to each of the plurality of reference sequences.

27. The method of clause 26, further comprising assigning, with the compute engine, one of a plurality of threat levels to each nucleotide sequence based upon the detection of whether hazardous content is present in that nucleotide sequence.

28. The method of clause 27, further comprising reporting, from the server to the frontend over the network, the threat level assigned to each nucleotide sequence of the one or more nucleotide sequences.

29. The method of any one of clauses 25-28, wherein comparing each nucleotide sequence of the one or more nucleotide sequences to each of the plurality of reference sequences comprises using a basic local alignment search tool (BLAST) to compare each nucleotide sequence to each of the plurality of reference sequences.

30. The method of any one of clauses 25-29, wherein each of the plurality of reference sequences includes hazardous content.

31. The method of clause 30, wherein the reference database further comprises metadata associated with each reference sequence that describes one or more characteristics of the hazardous content included in that reference sequence.

32. The method of clause 31, further comprising retrieving, with the compute engine, the corresponding metadata from the reference database in response to detecting that hazardous content is present in one of the nucleotide sequences.

33. The method of clause 32, further comprising reporting, from the server to the frontend over the network, the corresponding metadata for each nucleotide sequence for which hazardous content is detected.

34. The method of any one of clauses 26-33, wherein detecting whether hazardous content is present in each nucleotide sequence based upon the comparison of that nucleotide sequence to each of the plurality of reference sequences comprises selecting a reference sequence that provided a closest match to that nucleotide sequence during the comparison of that nucleotide sequence to each of the plurality of reference sequences, wherein the selected reference sequence includes hazardous content.

35. The method of clause 34, wherein detecting whether hazardous content is present in each nucleotide sequence based upon the comparison of that nucleotide sequence to each of the plurality of reference sequences further comprises detecting that hazardous content is present in that nucleotide sequence in response to determining that (i) a matching length between the selected reference sequence and that nucleotide sequence exceeds a threshold length and (ii) a matching percentage between the selected reference sequence and that nucleotide sequence exceeds a threshold percentage.

36. The method of any one of clauses 26-35, wherein detecting whether hazardous content is present in each nucleotide sequence based upon the comparison of that nucleotide sequence to each of the plurality of reference sequences comprises, for each reference sequence including hazardous content where (i) a matching length between the reference sequence and that nucleotide sequence does not exceed a threshold length but (ii) a matching percentage between the reference sequence and that nucleotide sequence does exceed a threshold percentage, extending the matching length up to the threshold length.

37. The method of clause 36, wherein detecting whether hazardous content is present in each nucleotide sequence based upon the comparison of that nucleotide sequence to each of the plurality of reference sequences further comprises detecting that hazardous content is present in that nucleotide sequence in response to determining that the matching percentage between the extended reference sequence and that nucleotide sequence still exceeds the threshold percentage.

38. The method of any one of clauses 26-37, wherein detecting whether hazardous content is present in each nucleotide sequence based upon the comparison of that nucleotide sequence to each of the plurality of reference sequences comprises, for each reference sequence including hazardous content where (i) a matching length between the reference sequence and that nucleotide sequence does exceed a threshold length but (ii) a matching percentage between the reference sequence and that nucleotide sequence does not exceed a threshold percentage, applying a sliding window to analyze a matching percentage between that nucleotide sequence and each portion of the reference sequence having the threshold length.

39. The method of clause 36, wherein detecting whether hazardous content is present in each nucleotide sequence based upon the comparison of that nucleotide sequence to each of the plurality of reference sequences further comprises detecting that hazardous content is present in that nucleotide sequence in response to determining that the matching percentage between that nucleotide sequence and any portion of the reference sequence having the threshold length exceeds the threshold percentage.

40. The method of any one of clauses 26-39, wherein detecting whether hazardous content is present in each nucleotide sequence based upon the comparison of that nucleotide sequence to each of the plurality of reference sequences comprises selecting a plurality of nucleotide sequence segments that each matched part of one of the plurality of reference sequences including hazardous content, where a matching length between each selected nucleotide sequence segment and the corresponding partial reference sequence does not exceed a threshold length.

41. The method of claim 40, further comprising combining the selected plurality of nucleotide sequence segments into a composite nucleotide sequence.

42. The method of claim 41, further comprising applying a sliding window to the composite nucleotide sequence to analyze a matching percentage between each portion of the composite nucleotide sequence having the threshold length and the one of the plurality of reference sequences.

43. The method of claim 44, further comprising detecting that hazardous content is present in the composite nucleotide sequence in response to determining that the matching percentage between any portion of the composite nucleotide sequence having the threshold length and the one of the plurality of reference sequences exceeds a threshold percentage.

44. The method of any one of clauses 24-43, further comprising providing a graphical user interface to allow a user to input the one or more nucleotide sequences to be screened for hazardous content and to display to the user the threat level assigned to each nucleotide sequence of the one or more nucleotide sequences.

45. The method of clause 44, wherein the graphical user interface is configured to allow the user to input a plurality of nucleotide sequences to be screened by uploading a single file containing the plurality of nucleotide sequences.

46. The method of clause 44 or clause 45, wherein the graphical user interface is configured to display to the user a progress of the screening of the one or more nucleotide sequences for hazardous content, based upon asynchronous updates received from the server, until the result is received from the server.

47. The method of any one of clauses 24-46, further comprising writing, with the server, each of the one or more nucleotide sequences received from the remote frontend to a queue stored in a workflow database including a queue of nucleotide sequences to be screened for hazardous content.

48. The method of clause 48, further comprising reading, with the compute engine, one nucleotide sequence at a time from the queue before comparing that nucleotide sequence to each of the plurality of reference sequences.

48. The method of any one of clauses 24-47, wherein the plurality of threat levels includes at least a first level representing a threat, a second level representing a potential threat, a third level representing an unlikely threat, and a fourth level representing a non-threat.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
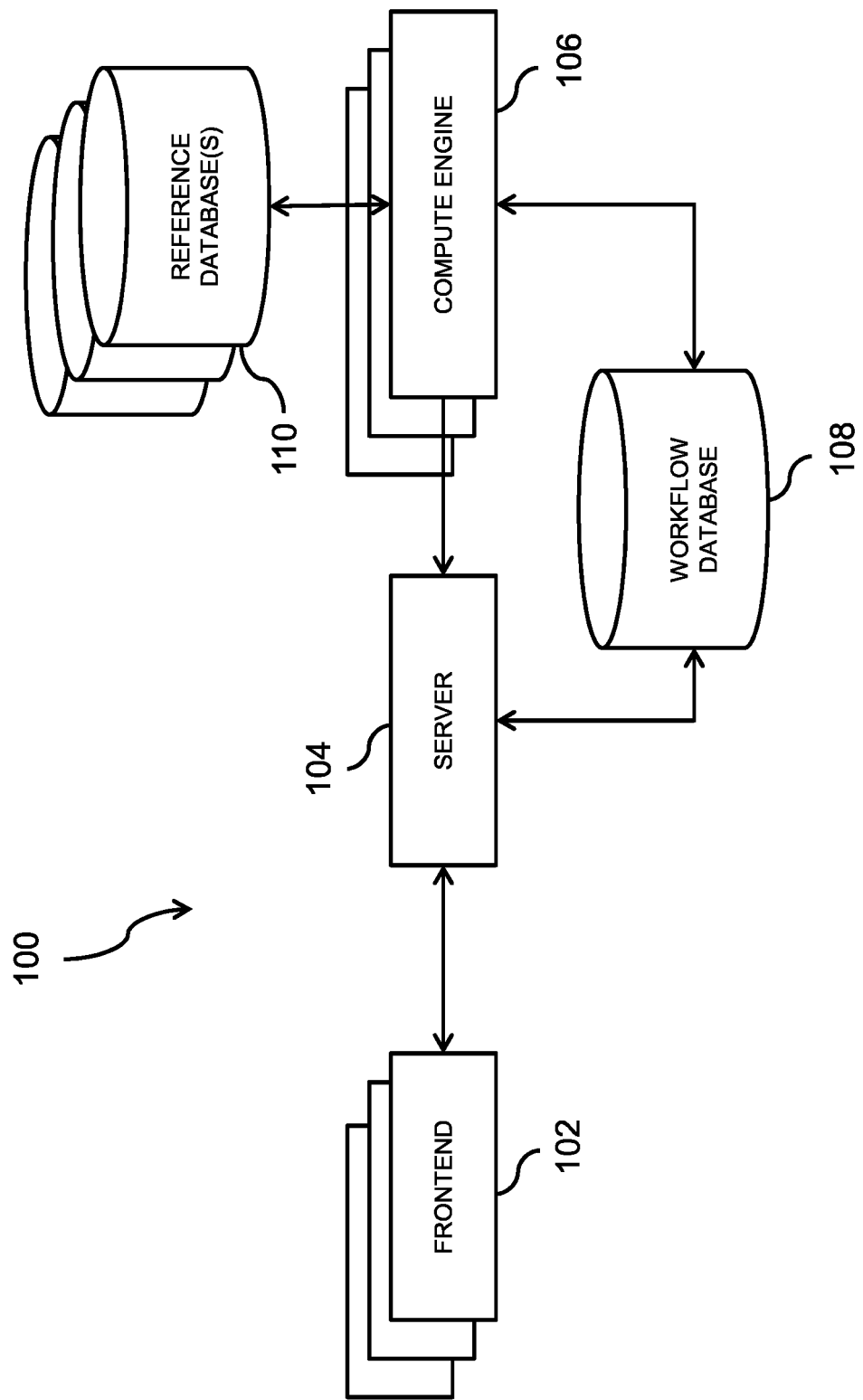
FIG. 1 is a simplified block diagram illustrating one embodiment of a system for nucleotide sequence screening.

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the concepts described herein may be implemented in hardware, firmware, software, or any combination thereof. For instance, embodiments of the concepts described herein may be implemented as data and/or instructions carried by or stored on one or more machine-readable or computer-readable storage media, which may be read and/or executed by one or more processors. A machine-readable or computer-readable storage medium may be embodied as any device, mechanism, or physical structure for storing or transmitting information in a form readable by a machine (e.g., a computing device or system). For example, a machine-readable or computer-readable storage medium may be embodied as read only memory (ROM) device(s); random access memory (RAM) device(s); magnetic disk storage media; optical storage media; flash memory devices; mini- or micro-SD cards, memory sticks, and others.

In the drawings, specific arrangements or orderings of schematic elements, such as those representing devices, modules, software, and data elements, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

In general, schematic elements used to represent software may be implemented using any suitable form of machine-readable instruction, such as software or firmware applications, programs, functions, modules, routines, processes, procedures, plug-ins, applets, widgets, code fragments and/or others, and that each such instruction may be implemented using any suitable programming language, library, application programming interface (API), and/or other software development tools. For example, some embodiments may be implemented using Java, C++, and/or other programming languages. Similarly, schematic elements used to represent data or information may be implemented using any suitable electronic arrangement or structure, such as a register, data store, table, record, array, index, hash, map, tree, list, graph, file (of any file type), folder, directory, database, and/or others.

Further, in the drawings, where connecting elements, such as solid or dashed lines or arrows, are used to illustrate a connection, relationship or association between or among two or more other schematic elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships or associations between elements. For example, where a connecting element represents a communication of signals, data, instructions, or other information, it should be understood by those skilled in the art that such element may represent one or multiple signal paths, as may be needed, to effect the communication.

Referring now to FIG. 1, one illustrative embodiment of a system 100 for nucleotide sequence screening is shown as a simplified block diagram. In this embodiment, the system 100 comprises a frontend 102, a server 104, a compute engine 106, a workflow database 108, and one or more reference databases 110. It is contemplated that the components of system 100 (including any of the frontend 102, the server 104, the compute engine 106, the workflow database 108, and the reference database(s) 110) may each be embodied in hardware, software, firmware, or any combination thereof. It will also be appreciated that, in some embodiments, the system 100 may include additional and/or different components than those shown in FIG. 1.

The various components of the system 100 are communicatively coupled via one or more wired and/or wireless networks (as illustrated by the arrows in FIG. 1). For example, the frontend 102, the server 104, the compute engine 106, the workflow database 108, and the reference database(s) 110 may each be communicatively coupled to some or all of the other components of the system 100 via a wired or wireless local area network (LAN), a wired or wireless wide area network (WAN), a cellular network, and/or a publicly-accessible, global network, such as the Internet. As such, the system 100 may include any number of additional components, such as additional computers, routers, and switches, to facilitate communications among the components of the system 100. Due to these network connections, it is not necessary for any of the components of system 100 to be physically located together. In the illustrative embodiment, the frontend 102 is located remotely from at least the server 104 (e.g., in another building, city, state, or country), and the frontend 102 and server 104 are communicatively coupled via the Internet.

In the illustrative embodiment, the frontend 102 provides a web interface through which a user of the system 100 can input one or more nucleotide sequences (e.g., DNA sequences) to be screened, can monitor progress of the screening of inputted sequences, and can view the results of completed screenings. The frontend 102 may be embodied as any type of computation or computer device capable of performing the functions described herein, including, without limitation, a computer, a multiprocessor system, a server, a rack-mounted server, a blade server, a programmable logic controller, an embedded controller, an embedded system, a processor-based system, and/or a consumer electronic device. The frontend 102 may alternatively be embodied as software and/or firmware configured to execute on any of the foregoing devices to perform the functions described herein. As suggested in FIG. 1, the system 100 may comprise numerous instances of the frontend 102 (e.g., associated with numerous users of the system 100).

In the illustrative embodiment, the server 104 receives requests for nucleotide sequence screening from the frontend 102, initiates new jobs based on such requests, tracks the progress of these jobs as they run, and reports results of completed screenings to the frontend 102. The server 104 may be embodied as any type of computation or computer device capable of performing the functions described herein, including, without limitation, a computer, a multiprocessor system, a server, a rack-mounted server, a blade server, a programmable logic controller, an embedded controller, an embedded system, a processor-based system, and/or a consumer electronic device. For example, the server 104 may be embodied as a web server accessible over a public network (e.g., a cloud server). Additionally or alternatively, the server 104 may be embodied as a local gateway device accessible over a local area network or other network. Additionally, in some embodiments, the server 104 may be embodied as a "virtual server" formed from multiple computing devices distributed across one or more networks and operating in a public or private cloud. Accordingly, although the server 104 is illustrated in FIG. 1 as embodied as a single server computing device, it should be appreciated that the server 104 may be embodied as multiple devices cooperating together to facilitate the functionality described below. In some embodiments (not shown) the server 104 and the compute engine 106 may both be embodied in the same physical server device or collection of devices.

In the illustrative embodiment, the compute engine 106 is embodied as an application for running comparisons between the nucleotide sequences being screened and reference sequences (stored in reference database(s) 110), analyzing the results of these comparisons to detect hazardous contents in the nucleotide sequences being screened, and updating the server 104 with its progress on these tasks. As suggested in FIG. 1, the system 100 may comprise numerous instances of the compute engine 106 (e.g., running on a cloud). The compute engine 106 may run on (or, alternatively, be embodied as) any type of computation or computer device capable of performing the functions described herein, including, without limitation, a computer, a multiprocessor system, a server, a rack-mounted server, a blade server, a programmable logic controller, an embedded controller, an embedded system, a processor-based system, and/or a consumer electronic device. For example, the compute engine 106 may be run on (or embodied as) a web server accessible over a public network (e.g., a cloud server). Additionally or alternatively, the compute engine 106 may run on (or be embodied as) a local gateway device accessible over a local area network or other network. Additionally, in some embodiments, the compute engine 106 may run on (or be embodied as) a "virtual server" formed from multiple computing devices distributed across one or more networks and operating in a public or private cloud. As noted above, in some embodiments (not shown), the server 104 and the compute engine 106 may both be embodied in (or run on) the same physical server device or collection of devices.

In the illustrative embodiment, the workflow database 108 is embodied as SQLite3 database for tracking jobs initiated by the server 104 and performed by the compute engine 106 and the results of those jobs once completed. The workflow database 108 may alternatively be embodied as any number of data structures stored on any type of computer-readable media. For instance, in some embodiments, the workflow database 108 may be combined with the server 104 and/or the compute engine 106.

The workflow database 108 illustratively maintains two tables of data. In a first data table, the workflow database 108 includes a queue of nucleotide sequences to be screened for hazardous content. Each entry in this table reflects a single nucleotide sequence to be run against a specific reference database 110 (by the compute engine 106). Each entry in the first data table of the workflow database 108 may include timestamps of when the run is started and when it is finished. This table may also group multiple runs (entries) together through the use of a "job identification" (job_id) field, without needing to create a separate table. Each entry in the first data table may also include an options field that contains a JavaScript Object Notation (JSON) encoded dictionary of options that may be passed to the compute engine 106 to influence how the run is handled. The workflow database 108 may also include a second data table to hold the results of the analyses performed by the compute engine 106. Additionally, each entry in this second table can specify the analysis performed by the compute engine 106 via "name" and "method" fields, by way of example.

Figure 3:
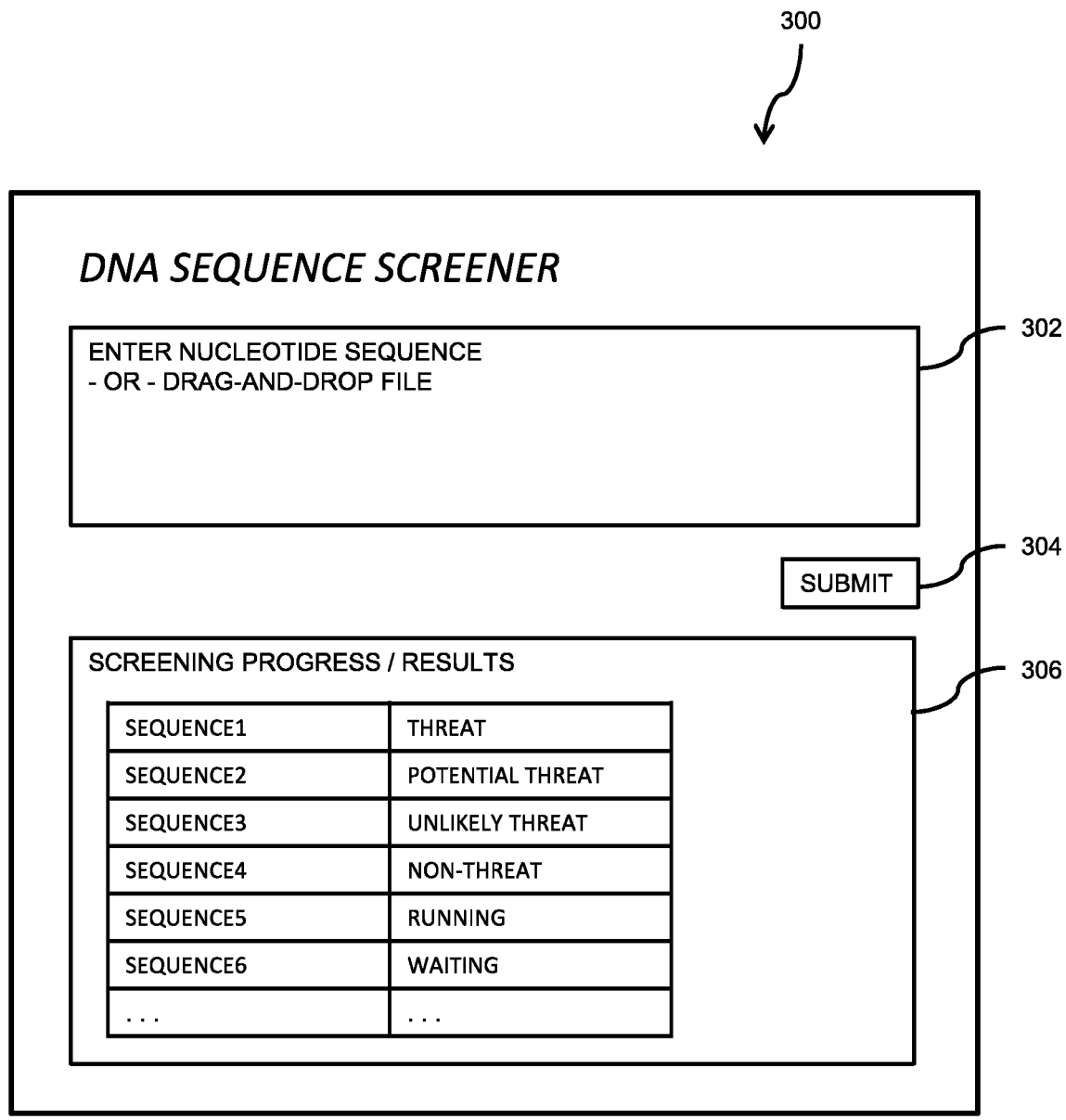
FIG. 3 is a simplified diagram illustrating one embodiment of a graphical user interface that may be provided by a frontend of the system of FIG. 1.

The frontend 102 is operable to provide a graphical user interface (GUI) 300, one simplified example of which is shown in FIG. 3. One working embodiment of this frontend 102 was built as a Single Page Web Application (SPA) using React, a javascript library for creating interactive user interfaces. As shown in FIG. 3, the GUI 300 includes an input box 302 that allows a user to input one or more nucleotide sequences to be screened for hazardous content. In this embodiment, the input box 302 allows a user to type sequences or copy-and-paste sequences to be screened. Additionally, the input box 302 allows for user to drag-and-drop text files containing nucleotide sequences (e.g., FASTA files) to upload them to the system 100 for screening. In this way, the user can easily input a large group of nucleotide sequences to be screened by uploading a single file.

The GUI 300 also includes a button 304 (labelled "submit" in FIG. 3) to complete the input process and begin the screening of any inputted sequences (whether manually typed into input box 302 or uploaded via a file). When a user clicks the "submit" button 304, a post request is sent to the server 104 to start the job. Pressing the button 304 also initiates the progress/results window 306 of the GUI 300.

The window 306 is utilized by the GUI 300 to display progress and/or results on each job submitted by a user of the frontend 102 of the system 100. When the window 306 is initiated (after button 304 is clicked), the frontend 102 opens a websocket connection to the server 104. As the frontend 102 receives asynchronous updates about the progress of the job from the server 104, the GUI 300 of the frontend 102 displays the progress to the user in window 306. For instance, in FIG. 3, the window 306 is displaying the status of the jobs entitled "Sequence5" and "Sequence6" as "running" and "waiting," respectively. Once the job is complete, the GUI 300 of frontend 102 displays the result of each screening to the user in window 306. As illustrated in FIG.

3, this result may take the form of a threat level assigned to each nucleotide sequence by the compute engine 106. In this illustrative embodiment, the threat level may take one of four values: "threat, "potential threat," "unlikely threat," and "non-threat." It will be appreciated that other threat levels (including different numbers of threat levels) might be used in other embodiments. In the illustrative embodiment, the portion of window 306 including the assigned threat level is also color coded to highlight the result (e.g., with greater threat levels being presented on red backgrounds of differing intensity and lesser threat levels being presented on green backgrounds of differing intensity).

The GUI 300 of the frontend 102 may also include a modal (not shown) for presenting additional results of the screening. This modal may become visible when a user clicks on or hovers the mouse over a particular portion of the GUI 300, such as the assigned threat levels in window 306. For instance, as described in more detail below, the reference database(s) 110 may include numerous types of metadata associated with each reference sequence, where the metadata describes one or more characteristics of the hazardous content included in that reference sequence. By way of example, the metadata might include a description of a Virulence Factor (VF) for the hazardous content, the VF's function, and the like. In such embodiments, this metadata may be retrieved from the reference database(s) 110 for nucleotide sequences hitting on these results and provide to the frontend 102 via the server 104. When a user of the GUI 300 clicks on one of the assigned threat levels in window 306 that indicates a threat, the modal may become visible ("pop-up") to display some or all of the metadata retrieved from the reference database(s) 110 relating to that nucleotide sequence and its hazardous content.

In one embodiment, the server 104 was implemented as a python webserver capable of handling Hypertext Transfer Protocol (HTTP) requests from the frontend 102 and the compute engine 106. In this embodiment, the server 104 implemented various endpoints, including an initiation endpoint, a notification endpoint, and a progress-monitoring endpoint. The initiation endpoint operates to receive one or more nucleotide sequences from the frontend 102 to be screened. This endpoint writes each sequence received to the queue (the first data table) maintained by the workflow database 108. The server 104 also specifies the analyses to be performed, including the reference database(s) 110 to be used, by the compute engine 106. This information is all stored in the workflow database 108 together with null fields to be filled in with results from the compute engine 106 upon the completion of each run.

The notification endpoint is used by the compute engine 106 to notify the server 104 whenever there is an update on the progress of a particular job. If there are any open websockets listening for the job ID associated with an update provided by the compute engine 106, the server 104 sends an update to the associated frontend 102. The websockets between the frontend 102 and the server 104 utilize the progress-monitoring endpoint. This endpoint adds the job ID associated with each open websocket to a list of IDs to monitor until the connection is no longer open. Whenever updates are triggered for a job with this ID, the server 104 will poll the workflow database 108 about all the runs and analyses associated with that ID. The server 104 compiles this information and sends it to the frontend 102 as an asynchronous update.

The compute engine 106 periodically polls the workflow database 108 for new runs and, when found, executes them. To do so, the compute engine 106 first compares the nucleotide sequence to a number of reference sequences stored in one of the reference databases 110. For instance, the compute engine 106 may access a reference database 110 that contains reference sequences known to include hazardous content (e.g., DNA sequences associate with disease, biological weapons, and the like). The compute engine 106 may compare the nucleotide sequence being run with each of the reference sequences using a basic local alignment search tool (BLAST) that identifies matching sequences within certain constraints, such as a certain percentage matching (a certain threshold of matching nucleotide bases) over a certain sequence length. The compute engine 106 may use any of the many known BLAST algorithms to perform this comparison. The workflow database 108 may specify which BLAST algorithm and/or reference database 110 are to be used for a particular run, or it may provide the compute engine 106 with data used to select an appropriate BLAST algorithm and/or appropriate reference database 110 to be used for a particular run. The workflow database 108 may also specify certain options (e.g., tolerances) to be used when running the BLAST algorithm to perform the comparisons.

After comparing the nucleotide sequence being run to the reference sequences of one of the reference databases 110, the compute engine 106 analyzes the results of the run to detect whether hazardous content is present in the nucleotide sequence and to assign one of a number of possible threat levels to the nucleotide sequence based upon this analysis. The compute engine 106 also retrieves a corresponding metadata associated with detected hazardous content from the reference database 110 and performs an necessary post-processing before returning the results to the workflow database 108 (e.g., aggregating match results into a historical database, or queueing a run against another database). The hazardous content detection algorithm (as well as the metadata retrieval and post-processing functions) used by the compute engine 106 can be specified by the "name" and "method" fields associated with each run in the workflow database 108.

In some embodiments, the compute engine 106 detects whether hazardous content is present in the nucleotide sequence by selecting a reference sequence that provided the closest match to the nucleotide sequence during the comparison of the nucleotide sequence to each of the plurality of reference sequences. The compute engine 106 then determines whether a matching length between the selected "closest match" reference sequence and the nucleotide sequence exceeds a threshold length and whether a matching percentage between the selected "closest match" reference sequence and the nucleotide sequence exceeds a threshold percentage. If the minimum length and percentage matching criteria are met, the compute engine 106 consider the nucleotide sequence to be a positive match to that reference sequence and flags the nucleotide sequence as containing whatever hazardous content is represented by the reference sequence.

In other embodiments, the compute engine 106 detects whether hazardous content is present in the nucleotide sequence by identifying each reference sequence where a matching length between the reference sequence and the nucleotide sequence does not exceed a threshold length but a matching percentage between the reference sequence and the nucleotide sequence does exceed a threshold percentage. For such a case, the compute engine 106 will extend (or scale) the matching length up to the threshold length determine whether the matching percentage between the extended reference sequence and the nucleotide sequence still exceeds the threshold percentage. If so, the compute engine 106 will consider the nucleotide sequence to be a positive match to that reference sequence and will flag the nucleotide sequence as containing whatever hazardous content is represented by the reference sequence.

In some embodiments, the compute engine 106 detects whether hazardous content is present in the nucleotide sequence by identifying each reference sequence where a matching length between the reference sequence and the nucleotide sequence does exceed a threshold length but a matching percentage between the reference sequence and the nucleotide sequence does not exceed a threshold percentage. For such a case, the compute engine 106 will apply a sliding window to analyze a matching percentage between the nucleotide sequence and each portion of the reference sequence having the threshold length. If the compute engine 106 determines that the matching percentage between the nucleotide sequence and any portion of the reference sequence having the threshold length exceeds the threshold percentage, it will consider the nucleotide sequence to be a positive match to that reference sequence and will flag the nucleotide sequence as containing whatever hazardous content is represented by the reference sequence.

In still other embodiments, the compute engine 106 may detect whether hazardous content is present in the nucleotide sequence by select a group of nucleotide sequence segments that each matched part of one of the reference sequences, but where a matching length between each selected nucleotide sequence segment and the corresponding partial reference sequence did not exceed a threshold length. In such a case, the compute engine 106 will combine the selected plurality of nucleotide sequence segments into a composite nucleotide sequence and apply a sliding window to the composite nucleotide sequence to analyze a matching percentage between each portion of the composite nucleotide sequence having the threshold length and the reference sequence. If the compute device determines that the matching percentage between any portion of the composite nucleotide sequence having the threshold length and the reference sequence exceeds the threshold percentage, the compute engine 106 will consider the composite nucleotide sequence to be a positive match to that reference sequence and will flag the nucleotide sequence as containing whatever hazardous content is represented by the reference sequence. This last approach catches cases where smaller segments of threat factors that would normally fail the threshold requirements are placed within a larger sequence. The compute engine 106 can apply this same approach to combine segments across all runs in a single job (not just a single run) as well.

Figure 2:
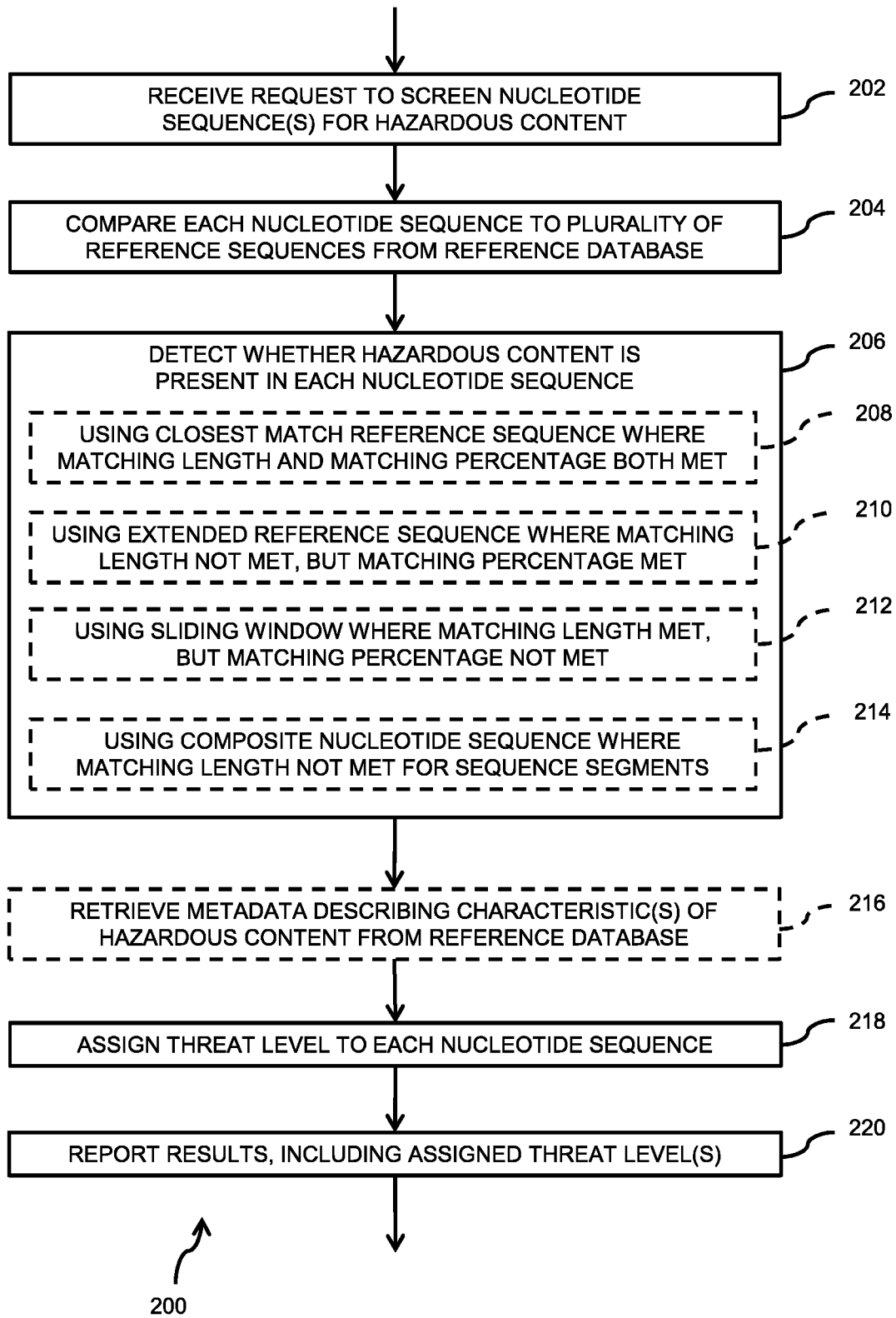
FIG. 2 is a simplified flow diagram illustrating one embodiment of a method of nucleotide sequence screening that may be performed by the system of FIG. 1.

Referring now to FIG. 2, one illustrative embodiment of a method 200 of nucleotide sequence screening is shown as a simplified flow diagram. The method 200 is illustrated as a number of blocks 202-220. Although the blocks 202-220 are generally shown and described sequentially in the present disclosure, it will be appreciated that the blocks 202-220 do not necessarily need to be performed in a particular order (unless otherwise noted below). For instance, it is contemplated that many of the blocks 202-220 might be performed in parallel with other blocks during the method 200.

The method 200 begins with block 202 in which the server 104 receives a request from the frontend 102 to screen one or more nucleotide sequences for hazardous content. As discussed above, the server 104 may receive this request and the associated nucleotide sequence(s) via the initiation endpoint. Block 202 may involve the server 104 writing the nucleotide sequence(s) to be screened to the queue in the workflow database 108.

After block 202, the method 200 proceeds to block 204 in which the compute engine 106 compares each nucleotide sequence of the one or more nucleotide sequences to each of a plurality of reference sequences stored in reference database 110. Block 204 may being with the compute engine 106 retrieving a nucleotide sequence to be screened from the queue maintained by the workflow database 108. During block 204, the compute engine 106 may use any suitable algorithm to compare the nucleotide sequence being run to the references sequences of one or more of the reference databases 110. In the illustrative embodiment, block 204 involves the compute engine 106 using a basic local alignment search tool (BLAST) to compare the nucleotide sequence to each of the reference sequences.

After block 204, the method 200 proceeds to block 206 in which the compute engine 106 detects whether hazardous content is present in each nucleotide sequence based upon the comparison of that nucleotide sequence to each of the plurality of reference sequences performed in block 202. Block 206 involves determining whether each nucleotide sufficiently matched one (or more) of the reference sequences including hazardous content. In this way, block 206 functions as a filter on the results of block 204 to find the matches that are true threats.

As discuss above, the detection of hazardous content in block 206 using the results of the comparisons from block 204 may take a number of forms in various embodiments. For instance, as represented in optional block 208, in some embodiments, the compute engine 106 detects whether hazardous content is present in the nucleotide sequence by selecting a reference sequence that provided the closest match to the nucleotide sequence during the comparison of the nucleotide sequence to each of the plurality of reference sequences. The compute engine 106 then determines whether a matching length between the selected "closest match" reference sequence and the nucleotide sequence exceeds a threshold length and whether a matching percentage between the selected "closest match" reference sequence and the nucleotide sequence exceeds a threshold percentage. If the minimum length and percentage matching criteria are met, the compute engine 106 consider the nucleotide sequence to be a positive match to that reference sequence and flags the nucleotide sequence as containing whatever hazardous content is represented by the reference sequence.

As represented in optional block 210, in other embodiments, the compute engine 106 detects whether hazardous content is present in the nucleotide sequence by identifying each reference sequence where a matching length between the reference sequence and the nucleotide sequence does not exceed a threshold length but a matching percentage between the reference sequence and the nucleotide sequence does exceed a threshold percentage. For such a case, the compute engine 106 will extend (or scale) the matching length up to the threshold length determine whether the matching percentage between the extended reference sequence and the nucleotide sequence still exceeds the threshold percentage. If so, the compute engine 106 will consider the nucleotide sequence to be a positive match to that reference sequence and will flag the nucleotide sequence as containing whatever hazardous content is represented by the reference sequence.

As represented in optional block 212, in other embodiments, the compute engine 106 detects whether hazardous content is present in the nucleotide sequence by identifying each reference sequence where a matching length between the reference sequence and the nucleotide sequence does exceed a threshold length but a matching percentage between the reference sequence and the nucleotide sequence does not exceed a threshold percentage. For such a case, the compute engine 106 will apply a sliding window to analyze a matching percentage between the nucleotide sequence and each portion of the reference sequence having the threshold length. If the compute engine 106 determines that the matching percentage between the nucleotide sequence and any portion of the reference sequence having the threshold length exceeds the threshold percentage, it will consider the nucleotide sequence to be a positive match to that reference sequence and will flag the nucleotide sequence as containing whatever hazardous content is represented by the reference sequence.

As represented in optional block 214, in still other embodiments, the compute engine 106 may detect whether hazardous content is present in the nucleotide sequence by select a group of nucleotide sequence segments that each matched part of one of the reference sequences, but where a matching length between each selected nucleotide sequence segment and the corresponding partial reference sequence did not exceed a threshold length. In such a case, the compute engine 106 will combine the selected plurality of nucleotide sequence segments into a composite nucleotide sequence and apply a sliding window to the composite nucleotide sequence to analyze a matching percentage between each portion of the composite nucleotide sequence having the threshold length and the reference sequence. If the compute device determines that the matching percentage between any portion of the composite nucleotide sequence having the threshold length and the reference sequence exceeds the threshold percentage, the compute engine 106 will consider the composite nucleotide sequence to be a positive match to that reference sequence and will flag the nucleotide sequence as containing whatever hazardous content is represented by the reference sequence. This last approach catches cases where smaller segments of threat factors that would normally fail the threshold requirements are placed within a larger sequence. In alternative embodiments of block 214, the compute engine 106 can apply this same approach to combine segments across all runs in a single job (not just a single run).

After block 206 (including any of optional blocks 208-214), the method 200 may optionally proceed to block 216 in which the compute engine 106 retrieves corresponding metadata from the reference database 110 in response to detecting that hazardous content is present in one of the nucleotide sequences. For instance, the reference database(s) 110 may include numerous types of metadata associated with each reference sequence, where the metadata describes one or more characteristics of the hazardous content included in that reference sequence. By way of example, the metadata might include a description of a Virulence Factor (VF) for the hazardous content, the VF's function, and the like.

After block 216 (when used), or after block 214 (if block 216 is not used), the method 200 proceeds to block 218 in which the compute engine 106 assigns one of a plurality of threat levels to each nucleotide sequence based upon the detection of whether hazardous content is present in that nucleotide sequence. Depending on how closely (or not) the nucleotide sequence being screened was determined to match one or more of the reference sequences including hazardous content in block 206, the nucleotide sequence may be assigned any of a first level representing a threat, a second level representing a potential threat, a third level representing an unlikely threat, or a fourth level representing a non-threat in block 218.

After block 218, the method 200 concludes with block 220 in which the compute engine 106 reports the result of screening the one or more nucleotide sequences for hazardous content to the frontend 102. In most embodiments, block 220 will involve the server 104 reporting the threat level assigned to each nucleotide sequence of the one or more nucleotide sequences to the frontend 102. Additionally, in some embodiments (where optional block 216 is utilized), block 220 may involve the server 104 reporting the corresponding metadata for each nucleotide sequence for which hazardous content is detected to the frontend 102. After receiving these results, the frontend 102 may display this information to a user using the GUI 300 (FIG. 3).

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A system for assessing threat levels associated with synthesizing nucleotide sequences, the system comprising:
    a server to communicate with a number of remote frontends over a network to receive, from the frontends, a number of requests to screen one or more nucleotide sequences to be synthesized for hazardous content, wherein the requests collectively include a plurality of nucleotide sequences; and
    a compute engine to:
        compare each nucleotide sequence of the plurality of nucleotide sequences to each of a plurality of reference sequences stored in a reference database, wherein the plurality of nucleotide sequences includes at least a thousand nucleotide sequences,
        detect whether hazardous content is present in each nucleotide sequence of the plurality of nucleotide sequences based upon the comparison of that nucleotide sequence to each of the plurality of reference sequences, including selecting a plurality of nucleotide sequence segments of the plurality of nucleotide sequences that each matches part of one of the plurality of reference sequences, in response to a determination that a matching length between each selected nucleotide sequence segment and the corresponding partial reference sequence does not satisfy a threshold length, combining the selected plurality of nucleotide sequence segments into a composite nucleotide sequence, and applying a sliding window to the composite nucleotide sequence to analyze a matching percentage between each portion of the composite nucleotide sequence having the threshold length and the one of the plurality of reference sequences, and assign one of a plurality of threat levels to synthesizing each nucleotide sequence based upon the detection of whether hazardous content is present in that nucleotide sequence;

wherein the server is further to report the threat level assigned to synthesizing each nucleotide sequence to the respective frontend that requested screening of that nucleotide sequence.

2. The system of claim 1, wherein to detect whether hazardous content is present in each nucleotide sequence based upon the comparison of that nucleotide sequence to each of the plurality of reference sequences comprises to:

select a reference sequence that provided a closest match to that nucleotide sequence during the comparison of that nucleotide sequence to each of the plurality of reference sequences, wherein the selected reference sequence includes hazardous content; and detect that hazardous content is present in that nucleotide sequence in response to determining that (i) a matching length between the selected reference sequence and that nucleotide sequence satisfies the threshold length and (ii) a matching percentage between the selected reference sequence and that nucleotide sequence satisfies a threshold percentage.

3. The system of claim 1, wherein to detect whether hazardous content is present in each nucleotide sequence based upon the comparison of that nucleotide sequence to each of the plurality of reference sequences comprises to:

for each reference sequence including hazardous content where (i) a matching length between the reference sequence and that nucleotide sequence does not satisfy the threshold length but (ii) a matching percentage between the reference sequence and that nucleotide sequence does satisfy a threshold percentage, extending the matching length up to the threshold length; and detect that hazardous content is present in that nucleotide sequence in response to determining that the matching percentage between the extended reference sequence and that nucleotide sequence still satisfies the threshold percentage.

4. The system of claim 1, wherein to detect whether hazardous content is present in each nucleotide sequence based upon the comparison of that nucleotide sequence to each of the plurality of reference sequences comprises to:

for each reference sequence including hazardous content where (i) a matching length between the reference sequence and that nucleotide sequence does satisfy the threshold length but (ii) a matching percentage between the reference sequence and that nucleotide sequence does not satisfy a threshold percentage, apply a sliding window to analyze a matching percentage between that nucleotide sequence and portions of the reference sequence having the threshold length; and detect that hazardous content is present in that nucleotide sequence in response to determining that the matching percentage between that nucleotide sequence and any portion of the reference sequence having the threshold length satisfies the threshold percentage.

5. The system of claim 1, wherein to detect whether hazardous content is present in each nucleotide sequence based upon the comparison of that nucleotide sequence to each of the plurality of reference sequences comprises to detect that hazardous content is present in the composite nucleotide sequence in response to determining that the matching percentage between any portion of the composite nucleotide sequence having the threshold length and the one of the plurality of reference sequences satisfies a threshold percentage.

6. The system of claim 1, wherein each of the plurality of reference sequences includes hazardous content, wherein the reference database further comprises metadata associated with each reference sequence that describes one or more characteristics of the hazardous content included in that reference sequence, and wherein the compute engine is configured to retrieve, in response to detecting that hazardous content is present in one of the nucleotide sequences, the corresponding metadata from the reference database, and wherein the server is further to report the corresponding metadata for each nucleotide sequence for which hazardous content is detected to the respective frontend that requested screening of that nucleotide sequence.

7. The system of claim 1, wherein the plurality of threat levels includes at least a first level representing a threat, a second level representing a potential threat, a third level representing an unlikely threat, and a fourth level representing a non-threat.

8. The system of claim 1, wherein to compare each nucleotide sequence of the plurality of nucleotide sequences to each of the plurality of reference sequences comprises using an alignment algorithm to compare each nucleotide sequence to each of the plurality of reference sequences.

9. The system of claim 1, wherein each frontend is to provide a graphical user interface to allow a user to input the one or more nucleotide sequences to be screened for hazardous content and to display to the user the threat level assigned to synthesizing each of the one or more nucleotide sequences input by the user.

10. The system of claim 9, wherein the graphical user interface is configured to allow the user to input multiple nucleotide sequences to be screened by uploading a single file containing the multiple nucleotide sequences.

11. The system of claim 9, wherein the graphical user interface is configured to display to the user a progress of the screening of the one or more nucleotide sequences for hazardous content, based upon asynchronous updates received from the server, until the threat level is received from the server.

12. The system of claim 1, further comprising a workflow database including a queue of nucleotide sequences to be screened for hazardous content, wherein the server is further to write each of the plurality of nucleotide sequences received from the frontends to the queue, and wherein the compute engine is further to read one nucleotide sequence at a time from the queue in order to compare that nucleotide sequence to each of the plurality of reference sequences.

13. A method for assessing threat levels associated with synthesizing one or more nucleotide sequences, the method comprising:

comparing, with a compute engine, each nucleotide sequence of the one or more nucleotide sequences to each of a plurality of reference sequences stored in a reference database;

detecting, with the compute engine, whether hazardous content is present in each nucleotide sequence of the one or more nucleotide sequences based upon the comparison of that nucleotide sequence to each of the plurality of reference sequences, including selecting a plurality of nucleotide sequence segments of the one or more nucleotide sequences that each matches part of one of the plurality of reference sequences, in response to a determination that a matching length between each selected nucleotide sequence segment and the corresponding partial reference sequence does not satisfy a threshold length, combining the selected plurality of nucleotide sequence segments into a composite nucleotide sequence, and applying a sliding window to the composite nucleotide sequence to analyze a matching percentage between each portion of the composite nucleotide sequence having the threshold length and the one of the plurality of reference sequences;

assigning, with the compute engine one of a plurality of threat levels to synthesizing each nucleotide sequence based upon the detection of whether hazardous content is present in that nucleotide sequence;

determining that a threat level assigned to a nucleotide sequence of the one or more nucleotide sequences does not represent a threat; and synthesizing, after determining that the threat level does not represent a threat, the nucleotide sequence of the one or more nucleotide sequences.

14. The method of claim 13, wherein detecting whether hazardous content is present in each nucleotide sequence based upon the comparison of that nucleotide sequence to each of the plurality of reference sequences comprises:

selecting a reference sequence that provided a closest match to that nucleotide sequence during the comparison of that nucleotide sequence to each of the plurality of reference sequences, wherein the selected reference sequence includes hazardous content; and detecting that hazardous content is present in that nucleotide sequence in response to determining that (i) a matching length between the selected reference sequence and that nucleotide sequence satisfies the threshold length and (ii) a matching percentage between the selected reference sequence and that nucleotide sequence satisfies a threshold percentage.

15. The method of claim 13, wherein detecting whether hazardous content is present in each nucleotide sequence based upon the comparison of that nucleotide sequence to each of the plurality of reference sequences comprises:

for each reference sequence including hazardous content where (i) a matching length between the reference sequence and that nucleotide sequence does not satisfy the threshold length but (ii) a matching percentage between the reference sequence and that nucleotide sequence does satisfy a threshold percentage, extending the matching length up to the threshold length; and detecting that hazardous content is present in that nucleotide sequence in response to determining that the matching percentage between the extended reference sequence and that nucleotide sequence still satisfies the threshold percentage.

16. The method of claim 13, wherein detecting whether hazardous content is present in each nucleotide sequence based upon the comparison of that nucleotide sequence to each of the plurality of reference sequences comprises:

for each reference sequence including hazardous content where (i) a matching length between the reference sequence and that nucleotide sequence does satisfy the threshold length but (ii) a matching percentage between the reference sequence and that nucleotide sequence does not satisfy a threshold percentage, applying a sliding window to analyze a matching percentage between that nucleotide sequence and portions of the reference sequence having the threshold length; and detecting that hazardous content is present in that nucleotide sequence in response to determining that the matching percentage between that nucleotide sequence and any portion of the reference sequence having the threshold length satisfies the threshold percentage.

17. The method of claim 13, wherein detecting whether hazardous content is present in each nucleotide sequence based upon the comparison of that nucleotide sequence to each of the plurality of reference sequences comprises detecting that hazardous content is present in the composite nucleotide sequence in response to determining that the matching percentage between any portion of the composite nucleotide sequence having the threshold length and the one of the plurality of reference sequences satisfies a threshold percentage.

18. The method of claim 13, wherein each of the plurality of reference sequences includes hazardous content, wherein the reference database further comprises metadata associated with each reference sequence that describes one or more characteristics of the hazardous content included in that reference sequence, and wherein the method further comprises retrieving, with the compute engine, the corresponding metadata from the reference database in response to detecting that hazardous content is present in one of the nucleotide sequences.

19. The method of claim 13, wherein comparing each nucleotide sequence of the one or more nucleotide sequences to each of the plurality of reference sequences comprises using an alignment algorithm to compare each nucleotide sequence to each of the plurality of reference sequences.

20. The method of claim 13, further comprising providing a graphical user interface to allow a user to input the one or more nucleotide sequences to be screened for hazardous content and to display to the user the threat level assigned to each nucleotide sequence of the one or more nucleotide sequences.

21. The method of claim 20, wherein the graphical user interface is configured to allow the user to input a plurality of nucleotide sequences to be screened by uploading a single file containing the plurality of nucleotide sequences.

22. The method of claim 20, wherein the graphical user interface is configured to display to the user a progress of the screening of the one or more nucleotide sequences for hazardous content.

23. The method of claim 13, further comprising:

writing each of the one or more nucleotide sequences to a queue stored in a workflow database including a queue of nucleotide sequences to be screened for hazardous content; and reading, with the compute engine, one nucleotide sequence at a time from the queue before comparing that nucleotide sequence to each of the plurality of reference sequences.

24. The method of claim 13, wherein the plurality of threat levels includes at least a first level representing a threat, a second level representing a potential threat, a third level representing an unlikely threat, and a fourth level representing a non-threat.

25. The system of claim 1, wherein the compute engine comprises a processor configured to compare each nucleotide sequence of the plurality of nucleotide sequences to each of a plurality of reference sequences stored in a reference database, detect whether hazardous content is present in each nucleotide sequence of the plurality of nucleotide sequences based upon the comparison of that nucleotide sequence to each of the plurality of reference sequences, and assign one of a plurality of threat levels to synthesizing each nucleotide sequence based upon the detection of whether hazardous content is present in that nucleotide sequence.

26. A system for assessing threat levels associated with synthesizing nucleotide sequences, the system comprising:
- a server to communicate with a remote frontend over a network to receive, from the frontend, a request to screen a plurality of nucleotide sequences to be synthesized for hazardous content and to report, to the frontend, a result of screening the plurality of nucleotide sequences to be synthesized for hazardous content, wherein the frontend is to provide a graphical user interface to allow a user to input the plurality of nucleotide sequences to be screened for hazardous content by uploading a single file containing the plurality of nucleotide sequences and to display to the user the result of screening the plurality of nucleotide sequences for hazardous content; and
- a processor to:
  - compare each nucleotide sequence of the plurality of nucleotide sequences to each of a plurality of reference sequences stored in a reference database, wherein the plurality of nucleotide sequences includes at least a thousand nucleotide sequences;
  - detect whether hazardous content is present in each nucleotide sequence of the plurality of nucleotide sequences based upon the comparison of that nucleotide sequence to each of the plurality of reference sequences, including selecting a plurality of nucleotide sequence segments of the plurality of nucleotide sequences that each matches part of one of the plurality of reference sequences, in response to a determination that a matching length between each selected nucleotide sequence segment and the corresponding partial reference sequence does not satisfy a threshold length, combining the selected plurality of nucleotide sequence segments into a composite nucleotide sequence, and applying a sliding window to the composite nucleotide sequence to analyze a matching percentage between each portion of the composite nucleotide sequence having the threshold length and the one of the plurality of reference sequences, and
  - assign one of a plurality of threat levels to synthesizing each nucleotide sequence based upon the detection of whether hazardous content is present in that nucleotide sequence;
- wherein the result reported to the frontend by the server comprises the threat level assigned to synthesizing each nucleotide sequence of the plurality of nucleotide sequences.

* * * * *